United States Patent [19]

Maerefat et al.

[11] Patent Number: 5,341,101
[45] Date of Patent: Aug. 23, 1994

[54] METHOD AND APPARATUS UTILIZING IONIZING AND MICROWAVE RADIATION FOR SATURATION DETERMINATION OF WATER, OIL AND A GAS IN A CORE SAMPLE

[75] Inventors: Nicida L. Maerefat, Sugar Land, Tex.; Ravi Parmeswar, Marlton, N.J.; Alan D. Brinkmeyer, Tulsa; Mehdi Honarpour, Bartlesville, both of Okla.

[73] Assignee: The United States of America as represented by the United States Department of Energy, Washington, D.C.

[21] Appl. No.: 50,977

[22] Filed: Apr. 20, 1993

Related U.S. Application Data

[63] Continuation of Ser. No. 649,536, Feb. 1, 1991, abandoned.

[51] Int. Cl.$^5$ .......................... G01V 3/12; G01V 5/00; G01N 22/00; G01N 23/00
[52] U.S. Cl. .................................. 324/376; 73/153; 250/255; 324/639; 324/640
[58] Field of Search .................... 324/376, 639–641; 73/38, 153; 250/253, 255

[56] References Cited

U.S. PATENT DOCUMENTS

| | | | |
|---|---|---|---|
| 4,486,714 | 12/1984 | Davis, Jr. et al. | 324/376 |
| 4,543,821 | 10/1985 | Davis, Jr. | 73/153 |
| 4,669,299 | 6/1987 | Closmann | 73/38 |

OTHER PUBLICATIONS

Maerefat, et al. "An Investigation Of Various Procedures To Determine Fluid Saturation in Three Phase Relative Permeability Measurements–Part I" (Feb. 19, 1985) Niper Report.

Parmeswar, et al. Niper-119 Topical Report "Design and Operation of the Three Phase Relative Permeability Apparatus (X-Ray/Microwave System)", Sep. 22, 1986.

Honarpour, et al. "Three-Phase Relative Permeability" (Draft Copy), Niper Reporting Period: Jan. 1–Mar. 31, 1989.

Model 1151 D Alphaline Differential Pressure Transmitter for a High Differentials, Rosemont, Inc. 1988. Product Date Sheet (no month).

Model 515 Power Supply, Rosemount Analytical Unilock Division, Mar. 1981. Brochure.

High Pressure Air Actuated Valve FV–103HA High Pressure, Three-Way Fluid Valve, Vindum Engineering, Prior to Feb. 1, 1991 (Brochure).

CV Series of High Pressure Valves, Vindum Engineering Brochure Prior to Feb. 1, 1991.

Newport Two-Wire Process-Loop Indicator in Nema-4 Housing Model 508A. Brochure Prior to Feb. 1, 1991.

(List continued on next page.)

*Primary Examiner*—Gerard R. Strecker
*Attorney, Agent, or Firm*—Mark P. Dvorscak; Hugh W. Glenn; William R. Moser

[57] ABSTRACT

A system for determining the relative permeabilities of gas, water and oil in a core sample has a microwave emitter/detector subsystem and an X-ray emitter/detector subsystem. A core holder positions the core sample between microwave absorbers which prevent diffracted microwaves from reaching a microwave detector where they would reduce the signal-to-noise ratio of the microwave measurements. The microwave emitter/detector subsystem and the X-ray emitter/detector subsystem each have linear calibration characteristics, allowing one subsystem to be calibrated with respect to the other subsystem. The dynamic range of microwave measurements is extended through the use of adjustable attenuators. This also facilitates the use of core samples with wide diameters. The stratification characteristics of the fluids may be observed with a windowed cell separator at the outlet of the core sample. The condensation of heavy hydrocarbon gas and the dynamic characteristics of the fluids are observed with a sight glass at the outlet of the core sample.

11 Claims, 8 Drawing Sheets

OTHER PUBLICATIONS

Maloney, et al. Niper–392 Topical Report "The Effects of Viscous Forces on Three–Phase Relative Permeability", Jan., 1989.

Oak, et al. "A New X–Ray Absorption Method for Measuring of Three–Phase Relative Permeability", SPE Petroleum Engineers 14420 (1985). (no month).

Honarpour, et al. "Three–Phase Relative Permeability", Niper Report, report period dated Oct. 1 through Dec. 31, 1988.

Honarpour, et al. "Three–Phase Relative Permeability Research" Niper Report, report period dated Jul. 1 through Sep. 30, 1988.

Honarpour, et al. "Three–Phase Relative Permeability Research" Niper Report, report period dated Apr. 1 through Jun. 30, 1988.

Parmeswar, et al., "Three–Phase Relative Permeability" Niper Report, report period dated Jul. 1 through Sep. 30, 1987.

Honarpour, et al., "Three–Phase Relative Permeability Research" Niper Report, report period dated Jan. 1 through Mar. 31, 1988.

Honarpour, et al., Status Report "The Effects of Viscous Forces on Three–Phase Relative Permeability" (May, 1988). IIT Research Institute Niper.

METHOD AND APPARATUS UTILIZING IONIZING AND MICROWAVE RADIATION FOR SATURATION DETERMINATION OF WATER, OIL AND A GAS IN A CORE SAMPLE

This invention was made with Government support under Contract No. DE-FC22-83FE60149 awarded by the Department of Energy. The Government has certain rights in this invention.

This application is a continuation of application Ser. No. 649,536 filed Feb. 1, 1991, now abandoned.

BACKGROUND OF THE INVENTION

The invention relates to a method and an apparatus for making measurements of gases and liquids in a core sample. In particular, the invention relates to a method and apparatus for determining simultaneously the saturation of oil, water and a gas in a geological sample.

As the cost of petroleum has increased due in part to the decrease in available domestic supplies of petroleum, it has become economically attractive to extract petroleum from fields which might have been considered to be unproductive a number of years ago. Today, petroleum may be extracted through various tertiary recovery methods or enhanced oil recovery (EOR) methods such as fire flooding, steam flooding, carbon dioxide flooding, by pumping surfactants into geological formations and the like. In addition, solution gas drive, gas cap pressure drive and other methods may be used. It is important to the practice of any of these methods that the characteristics of the geological formation in which the petroleum is located be determined as accurately as possible. In many instances, a selected geological formation which is a potential candidate for tertiary petroleum recovery may contain water, usually in the form of brine; petroleum including crude oil containing mixtures of various light and heavy fractions of hydrocarbons; and gas, which may include natural gas consisting primarily of methane ($CH_4$).

In a typical secondary or tertiary recovery technique pressure is applied to one or more sites in a region of a potential recoverable field. The pressure forces the petroleum to locations from which it may be pumped out of the ground via wells, etc. In some instances, if the geological formation is highly permeable to a gas such as steam, carbon dioxide, nitrogen or the like, its use may cause failure of the recovery process because the gas will tend to break through or "finger" that is, form a narrow column to the well bore where it is exhausted into the atmosphere without driving the petroleum to the well bore for recovery. This, of course, diminishes if not prevents recovery of the petroleum from the site. If fire flooding techniques are used without having determined the permeability of the geological formation to oil, gas and water, gaseous combustion products of the petroleum also may be vented directly to the atmosphere without forcing the remaining petroleum to move toward the well bore, consuming the petroleum to no good end.

It is therefore important to determine if possible, the relative permeability of the geological formation in which the oil is found. In particular, it is important to determine the relative permeability of the formation for gas, oil and water so that when pressure is applied to the petroleum in the formation, usually by means of a gas, it can be determined whether there is a likelihood that fingering might occur with possible loss of the oil to be recovered.

In the past, laboratory measurements of three-phase relative permeabilities for steady state and unsteady state conditions in core samples have been somewhat inaccurate. In the reported data, in most cases, there was considerable data scatter, which was classified by most researchers as characteristic of three-phase permeability measurements. Most prior art studies employed some type of data smoothing or curve fitting techniques in order to draw meaningful conclusions from the relatively scattered data. Many of those studies indicated that end effects on the cores whose permeability was being measured significantly perturbed the relative permeability measurements. As a result, the regions of the cores within which the three-phase measurements could be made were shown to be quite small. Some researchers have shown that the relative permeability of each of the oil, water and gas phases was a function of its own saturation, whereas other researchers concluded that the permeability of each phase was a function of all three saturations. In most cases, however, relative permeability to water or brine was reported to be a function of brine saturation alone. Oil relative permeability was thought to be a function of the saturations of oil, gas and water. The relative permeability to gas is interpreted either as being solely dependent upon the gas itself or upon the permeability of the oil, water and gas because the observed effects were too small to be considered to be statistically significant when compared to the experimental error. Relative permeability curves could not be described conclusively from published data. Some studies showed relatively large curvatures between 0% and 100% saturation. The curvature in the portions of the graphs where all three phases were indicated to be flowing was rather limited. If the data points were curve-fitted, excluding points outside the three-phase flow region, a straight line also could be fitted to the data within the limits of experimental accuracy. Further, when the saturation of the fluid was found to be lower than the residual saturation, a change in wettability might take place.

It was also found that hysteresis played an important role in unsteady state tests but only had a negligible effect on steady state determinations. The viscosity of the non-wetting phases, such as the oil, had little effect on three-phase relative permeability. However, the viscosity of the wetting phase, in this instance brine, had a substantial effect.

It was found that three-phase relative permeability tests are relatively prone to experimental errors. The most common reported problems, thus, are related to end effects, hysteresis, inaccurate saturation determinations and wettability changes. These problems generally result in considerable scatter of the data points which make the data difficult to interpret using relatively simple statistical techniques, such as manual techniques. Multi-variate interpolation and curve-fitting techniques are required by the data scatter, however, the curves resulting from the use of these techniques usually have the problem of not being unique. Also, the region of the diagrams in which all three phases are found to be flowing is quite limited making it difficult to predict trends. The above problems make it necessary to carefully design methods and apparatus for determining three-phase relative permeability.

In order to define three-phase relative permeability characteristics completely, six separate sets of unsteady state experiments are usually needed to describe all possible displacement histories. However, the time needed for completing a set of six unsteady state runs may still be less than a single steady state test. The possibility of wettability alterations during cleaning and drying and the resaturation of the core being tested and the resulting amounts of time needed to resaturate the core during each of the 6 sets of runs may be relatively large. Moreover, the fluid displacement tests are more prone to core heterogeneities and fluid front instabilities which are difficult to monitor and quantify. Steady state results, however, are less sensitive to hysteresis and tend to approach an average of the drainage and imbibition characteristics of the core being sampled. The steady state technique, therefore, would appear to be more attractive from the standpoint of determining core characteristics.

In U.S. Pat. No. 4,486,714 to Davis, Jr. et al. for Method and Apparatus for Measuring Relative Permeability and Water Saturation of a Core of Earthen Material a two-phase oil and water mixture is injected into an earthen core. Microwave energy is passed through the core while the liquid mixture is flowed through it under pressure. The pressure drop is determined along the length of the core. The relative permeabilities of the oil and water fractions, as well the water saturation of the core, are determined from the flow rate of the liquid mixture, the received microwave energy intensity and the pressure drop across the core.

Similarly U.S. Pat. No. 4,543,821 to Davis, Jr. for Method and Apparatus for Measuring Relative Permeability and Water Saturation of a Core teaches a system for determining the oil and water permeability of a core and its water saturation in a fashion similar to that in Davis, Jr. et al. primarily by means of measuring the amount of microwave energy transmitted through the core which indicates the amount of water in the core absorbing the microwave energy.

Parsons, R. W. "Microwave Attenuation—A New Tool For Monitoring Saturations And Laboratory Flooding Experiments" Society of Petroleum Engineers Journal, August, 1975, discloses a method for determining the amount of water in a core by measuring the absorption of microwave radiation by the electrical dipoles of the water molecules. It may be appreciated that the discussion points that most gases and liquids have negligible loss factors at microwave frequencies, water being an exception.

In another type of system the relative permeabilities of two materials may be determined by means of X-ray absorption measurements, Oak, M. J. and Ehrlich, R., "A New X-ray Absorption Method For Measurement of Three-Phase Relative Permeability", Society of Petroleum Engineers (1985) SPE-14420 discloses a system wherein X-ray absorption is measured for a three-phase system. The absorption is measured at X-ray potentials between 33 kilovolts and 45 kilovolts. It should be noted that the three-phase system consists of water, oil and gas both the water and oil phases having a specific tracer or X-ray absorption media associated therewith. The X-ray absorption equipment specifically uses scintillation measuring techniques to selectively measure X-ray intensities at each of two wavelength bands for which band splitting is provided by an iodine filter. Electric pulses generated by the X-ray photons in the scintillation counter are received by pulse height analyzers or selectors so that X-ray photons belonging to the separate wavelength bands corresponding to the two absorption regions may be distinguished.

U.S. Pat. No. 4,669,299 to Closman for Measuring Relative Permeability to Steam in Cores of Water and Oil Containing Reservoir Formations is directed to an X-ray scanning technique for sealed cores for determining the saturation from the density of tagged oil volumes and the permeability of the core from the densities in combination with measured pressures and temperatures.

Unfortunately, the prior art systems suffer from several defects. Both the Oak, et al. and Closman X-ray systems require that the material which absorbs the X-rays be associated with the water or oil, thus the liquid phases must be tagged in the event that three-phase measurements are to be made for a pair of liquid phases and a gas phase; each of the liquid phases must be tagged with a separate absorber. The use of absorbers, however, changes the relative saturation and permeability of the core because of changes in the surface interactions between the interior surfaces of the core and the tag liquids. Thus, as additional tagging agents are used the measured behavior of the core departs from the in situ behavior of the core exposed only to pure oil, brine and gas. As a result, the X-ray systems which tag both of the liquid phases perturb the saturation and permeability measurements.

The microwave measurements of the type disclosed in Davis, Jr. et al., Davis, Jr., and Parsons do not require the use of a tag medium. Oil and gas, however, have substantially the same absorption for microwave radiation, practically nil. Thus, it is almost impossible, using only microwave determinations, to determine whether the remaining volume of the core sample is primarily oil or gas. While gravimetric methods may be used to determine mass changes as the core is dried or filled with fluid, only relatively small changes occur and if the densities of the two fluids are relatively close, it is impossible to determine how much oil is present in the core sample.

It would be desirable to configure an apparatus for the determination of the saturation water, oil, and gas in a way which utilizes both X-ray and microwave radiation. In so doing, water measurements can be made independent of oil measurements. The microwave system could be utilized to measure water saturation without the need to tag the water while the X-ray system could be utilized to measure tagged oil. Since the oil would be the only liquid tagged with an absorber, changes in the relative saturation and permeability of the core would be minimal. The X-ray absorption by water remains practically nil and the microwave absorption by the oil also remains practically nil. Thus, the microwave and X-ray systems act independent of each other. Moreover, the use of two fluid measurement systems in one apparatus could facilitate the calibration of one system from the other. Unfortunately, the prior art systems have not been able to utilize such a calibration scheme due to difficulties associated with establishing a linear calibration line to relate the X-ray energies to microwave energies or the microwave energies to X-ray energies.

It is also desirable and necessary to make fluid measurements over a broad dynamic range of possible values for saturation and permeability levels. The desire to make three-phase steady state measurements makes this requirement even more crucial and difficult. When three fluid phases coexist in one core sample, naturally saturation levels may swing from practically nil to high saturation levels in a given area of the core sample. This presents a particular problem when measurement devices can only measure accurately over a relatively narrow range of values. The use of lanthanum X-ray targets and iodine tagging in X-ray systems for measuring oil saturations have adequately dealt with this problem and this is taught by the prior art. However, microwave detectors used to measure water levels typically have a limited dynamic measurement range. The ability to circumvent this problem associated with microwave measurements would enable one to accurately measure water saturation levels in a three-phase system. Moreover, measurements on cores with wider diameters would also be facilitated by such a system.

It would be further desirable to simulate actual reservoir conditions by elevating the temperature and pressure of the core sample. This is known to have the effect of causing condensation of heavy hydrocarbon gas or wet gas. Since in situ condensation affects overall three-phase permeabilities, the ability to measure condensation under real temperature and pressure conditions more accurately determines the three-phase permeability characteristics of a core sample.

It is still further desirable to visually monitor fluid characteristics and flow patterns through the core sample. The ability to do so would provide feedback as to whether the measurement system is providing realistic information about core permeabilities.

SUMMARY OF THE INVENTION

The instant invention solves a number of the problems of the prior art by enabling one to examine the characteristics of a core as three materials are flowed through it—gas, water and oil. A moving bed system carrying an X-ray generator and receiver in proximity with a microwave generator and receiver simultaneously determines the amount of tagged oil by X-ray absorption methods and water by microwave absorption methods. Thus allowing specific measurements of the two liquid phases to be made so that one can easily calculate by graphometry methods the portion of the core occupied by the gas.

In particular, the system employs an X-ray transmitter and receiver operating under the control of a computer to provide rapid and dynamic determinations of the X-ray absorption along the length of a core as tagged oil, water and gas are being supplied to it in known relative quantities. The amount of water may quickly and easily be determined by feeding the microwave absorption signal to a thermocouple detection which generates a signal for a computer. The computer rapidly computes the saturation of the core from the X-ray and microwave absorption, as well as from pressure drops measured along the core and known flow rates of gases and liquids delivered to the inlet of the core.

It is a principal aspect of the present invention to provide a three-phase saturation measurement system which can simultaneously determine the amount of tagged oil and untagged water by direct measurement in a porous geological core.

It is another aspect of the present invention to provide a three-phase measurement system wherein real time simultaneous measurements can be made of the quantity of tagged oil and untagged water in a core and thereby calculate the amount of gas also present in a core.

It is further aspect of the present invention to provide a three-phase measurement system wherein a relationship defining a linear calibration line between the microwave system and the X-ray system can be determined to calibrate each system against the other.

It is a still further aspect of the present invention to provide a three-phase measurement system which provides accurate measurements over a broad dynamic range of possible values by adjustably attenuating the microwave radiation.

It is a further aspect of the present invention to provide a three-phase measurement system which measures in situ heavy hydrocarbon condensation under simulated reservoir temperature and pressure conditions by utilizing a windowed sight glass.

It is a further aspect of the present invention to provide a three-phase measurement system which monitors the dynamic characteristics of the liquids by using a windowed cell separator.

These and other aspects and uses of the present invention will become apparent to one of ordinary skill in the art upon a perusal of the following specification and claims in light of the accompanying drawings, which are provided in an apparatus for determining the amounts of water, oil and gas in a core sample, the core sample having a matrix defining an open space occupied by water, oil and gas, the apparatus comprising means for illuminating an area of said core sample with focused microwave radiation of a known intensity, means for adjustably attenuating the microwave radiation to ensure that the power level of the microwave radiation emerging from said core sample is within a measurable range, means for measuring the microwave radiation emerging from the core sample to determine the amount of water in the core sample, a core holder having microwave absorptive material at least partially surrounding a core sleeve holding the core sample for absorbing microwave radiation diffracted around the core sleeve and preventing the diffracted microwave radiation from being detected by the means for measuring, means for illuminating an area of the core sample with ionizing electromagnetic radiation (or X-ray radiation) of a known intensity simultaneously with the microwave radiation, means for measuring said amount of ionizing electromagnetic radiation transmitted through the core sample to determine the amount of oil in the open space or void of the core sample, comparing means, interfaced with the means for measuring microwave radiation and the means for measuring ionizing radiation, for comparing a void volume of said core sample, previously derived by saturating the lone sample either with built in tagged oil and measuring the microwave or x-ray absorption, to the amount of oil and brine when gas is also present to determine the amount of gas occupying portions of said void space or volume not occupied by the water and the oil, means for optically examining the condensation of heavy hydrocarbon gas and the oil and water fluid components inside said core sample, and means for optically examining the stratification of the fluids inside the core sample.

DETAILED DESCRIPTION OF THE PREFERRED EMBODIMENT

Figure 1:
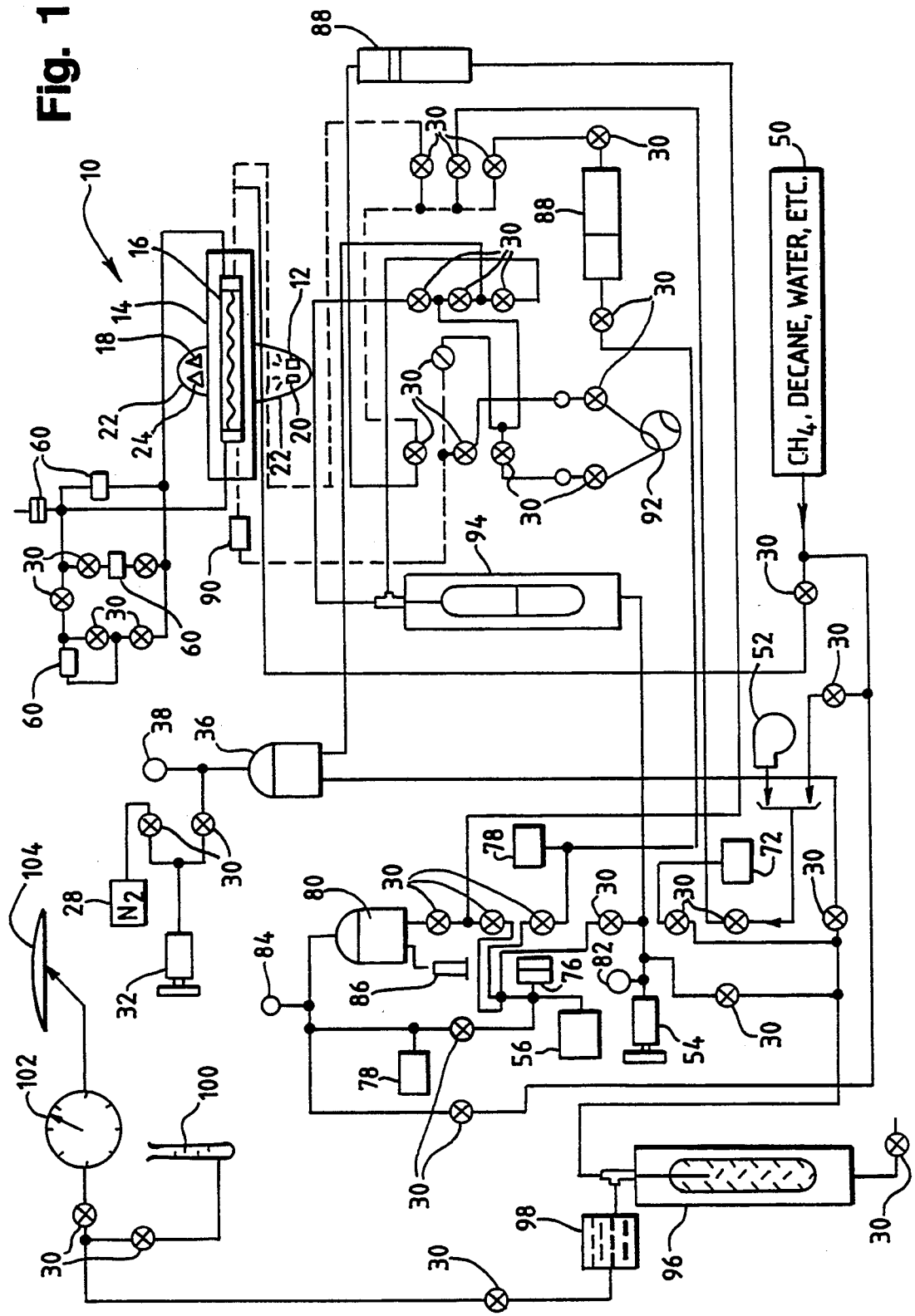
FIG. 1 is a schematic diagram of an apparatus for measuring relative saturation of oil, water and gas in a core sample, showing details of its fluid handling apparatus.
Figure 2:
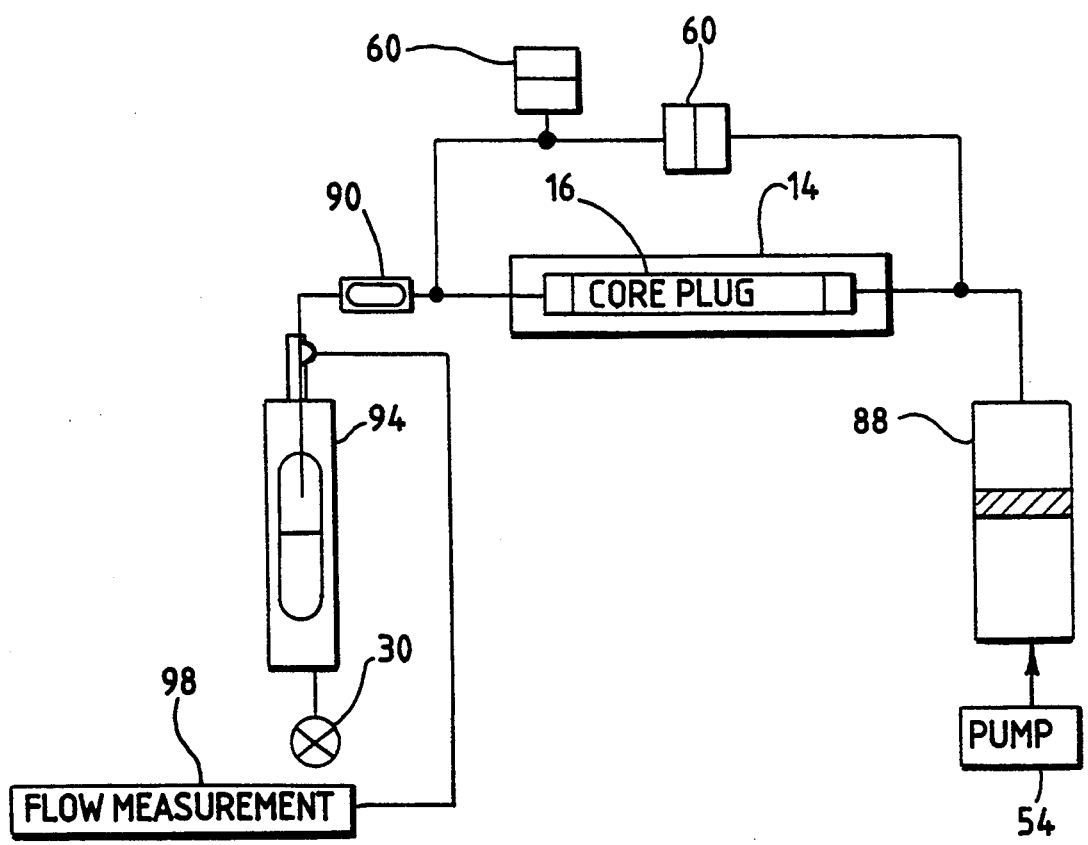
FIG. 2 is a simplified schematic diagram of the apparatus shown in FIG. 1 for measuring relative saturation of oil, water and gas in a core sample.
Figure 3:
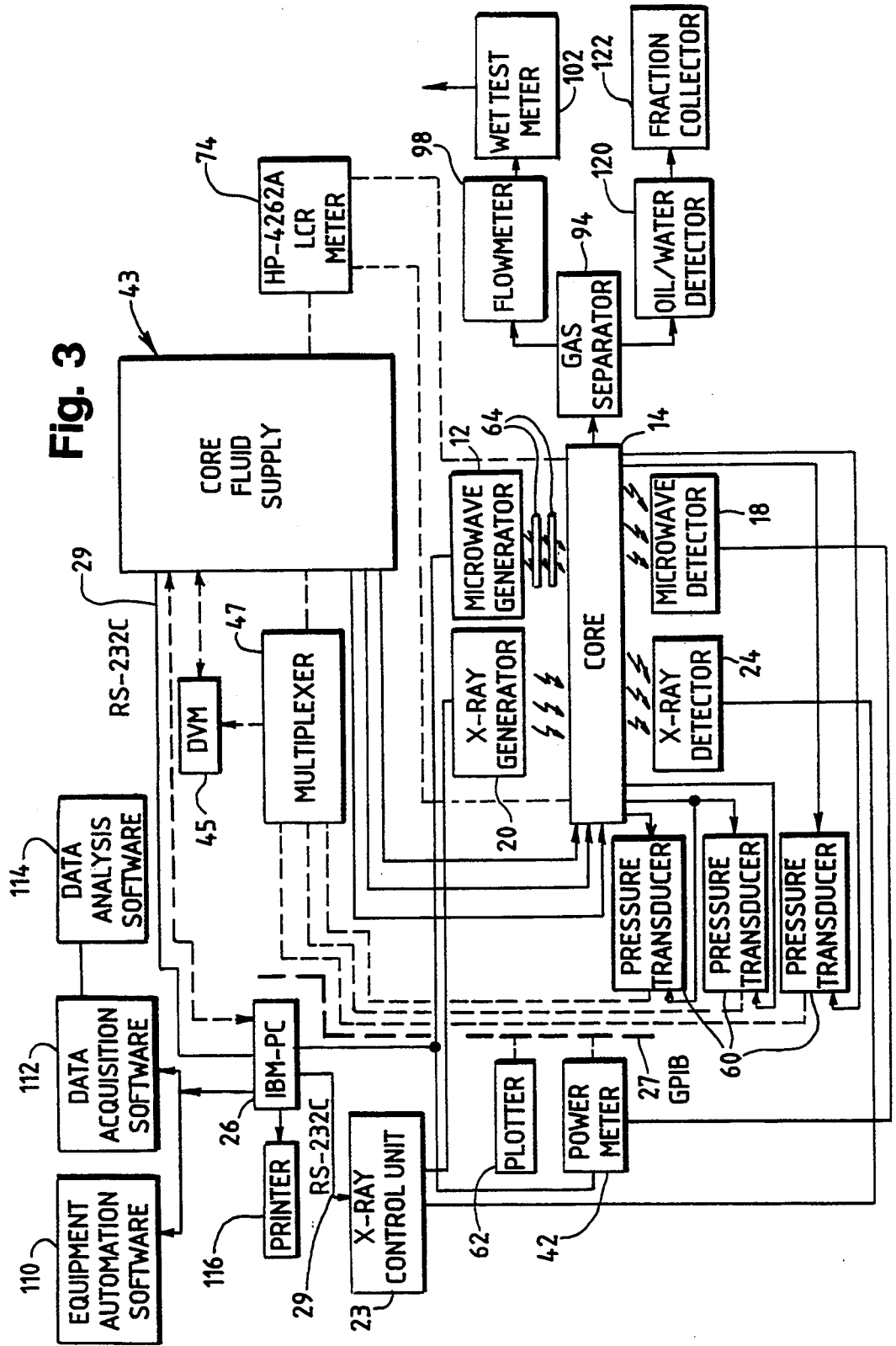
FIG. 3 is a block logic diagram of the apparatus of FIG. 1, showing details of its signal handling apparatus, for measuring relative saturation of oil, water and gas in a core sample.

Referring now to the drawings and initially to FIGS. 1, 2 and 3, an apparatus 10 for measuring the relative saturations of oil, gas and water in a core sample embodying the present invention is shown therein. The apparatus 10 includes means for illuminating microwave radiation comprising a microwave emitter 12 for illuminating a shielded core holder 14 containing a core sample or core plug 16. Means for measuring microwave radiation comprising a microwave detector 18 is located opposite the illumination means 12 and measures the amount of microwave radiation emerging from the core sample 16 to determine an amount of water in the core sample 16. The microwave detector 18 measures the microwave radiation emanating from the core sample 16 due to the illumination provided by the microwave emitter 12 and produces a microwave power level signal responsive to the amount of microwave received by the microwave detector 18. A power meter 42 is connected to the microwave detector 18 to receive the microwave power level signal and provides an output indication thereof. The power meter 42 is a Hewlett Packard Model 438A microprocessor-controlled dual channel meter. Channel A is configured to measure microwave input power and channel B is configured to measure microwave output power. The microwave technique using microwave emitter 12 and microwave detector 18 is selected for brine or water saturation measurements because it does not require the use of a tagging agent in the water. This technique has been shown to be effective for three-phase relative permeability experiments.

The low sensitivity of the microwave detector 18 creates dynamic range limitations on the microwave measurements. Thus, an aspect of this invention, is to broaden the dynamic measurement range by using microwave attenuators 64 as illustrated in FIG. 3. The attenuators 64 used are manufactured by Systron Donner, Model DBE-430. The attenuators 64 maintain the power level of the microwaves emanating from the core holder 14 within the maximum range detectable by the microwave detector 18. The microwave detector 18 measures microwave signals in the range of 100 pW to 10 μW. In addition to providing a means to detecting a broad dynamic range of potential water saturation levels, the microwave detector/emitter scheme using attenuators, allows the apparatus 10 to measure the permeabilities of core samples as wide as 2 inches. The microwave emitter 12 also uses lens corrected microwave horns to increase the accuracy of the measurements. The lens corrected horns focus the microwave to a beam width of one centimeter on the core sample 16. The lens corrected microwave horns also prevent the microwave radiation from scattering around the core sample 16.

The microwave detector 18 used in the present embodiment is a Hewlett Packard Model 8485A which detects microwave power by using a thin-film thermocouple detector. The power meter 42 in conjunction with the microwave detector 18 facilitates the measurement of the microwave power by amplifying the electromotive force provided by the microwave detector 18 to a usable level, which is directly related to the microwave power. This information is then transferred to an information analyzing means, an IBM personal computer 26, via a standard GPIB bus 27 (general purpose interface bus). The computer 26 is equipped with a National Instruments GPIB-PC IEEE-488 interface board which allows the computer 26 to receive data and trigger specific devices which are compatibly interfaced with the GPIB bus 27. The computer 26 also communicates with peripherals through a RS-232C channel 29. The microwave absorption measurement technique is based on the microwave energy absorbed by water molecules. A profile of the amount of water contained inside the core 16 is derived by relating microwave signal loss through the core 16 to the absorption of the microwave radiation by water. The relationship between the microwave signal loss and water saturation is defined by the Beer-Lambert law:

$$\text{LOG}\frac{I}{I_i} = A = -\frac{K_a\,Ch}{2.303} \qquad (1)$$

where:
 I = radiation intensity entering the sample,
 $I_i$ = radiation intensity emerging from sample,
 $K_a$ = molar absorption coefficient = $(4pfKf_v)/cC$
 $f_v$ = volume fraction of absorber, molarity,
 h = thickness of sample,
 C = concentration of absorber,
 K = extinction coefficient,
 f = radiation frequency,
 c = velocity of light in vacuum, and A = absorbance.
ρ = density Turning now to FIGS. 5 and 6, a means for illuminating ionizing electromagnetic radiation or an X-ray emitter 20 is mounted on a movable table 22 along with the microwave emitter 12 and the microwave detector 18. In the present embodiment X-rays are the preferred ionizing electromagnetic radiation. A means for measuring ionizing electromagnetic radiation or an X-ray detector 24 is located opposite the ionizing electromagnetic radiation emitter 20, with the core holder 14, containing the core sample 16, positioned therebetween. An X-ray control unit 23 controls the X-ray generator and the X-ray detector 24. The X-ray detector 24 produces an X-ray core intensity profile signal corresponding to the intensity of the X-rays illuminating the core sample 16 and the amount of iodine tagged oil contained in the core sample 16.

X-ray absorption techniques have been used in the past. Basically, since X-rays are attenuated very little by oil, iododecane or any other iodine compound which dissolves in oil and increases the absorption of the oil to X-rays may be used to tag the oil. This provides a means to detect the oil with X-ray radiation. A profile of the amount of oil contained inside the core 16 is derived by relating X-ray signal loss through the core 16 to the absorption of the X-ray radiation by the iodine tagged oil. The relationship between the X-ray signal loss and oil is also defined by the Beer-Lambert law.

The X-ray emitter 20 is part of an X-ray system manufactured by Phillips Electronic Instruments Inc. A high voltage generator supplies the X-ray tube with high voltage and filament currents. The X-ray tube has a maximum power rating of 3500 watts. The X-ray tube and the X-ray generator are water cooled to prevent overheating and to ensure a longer life span for these components.

The X-ray detector 24 is a scintillation counter. This counter tube converts incident X-ray quanta into electronic pulses. The X-ray detector 24 is also referred to as a pulse height analyzer (PHA). The pulses generated are then amplified by a preamplifier and passed onto a measuring channel. The measuring channel is composed of a linear amplifier and a pulse height analyzer or discriminator.

A lanthanum target X-ray tube is used because it produces two, high-intensity fluorescent beams which have an energy spread of only 0.4 KeV on either side of the iodine K-absorption edge. This enhances the ability of the apparatus 10 to detect the iodine tagged oil in the core 16 with X-ray radiation. Additionally, polychromatic effects which disturb the proportionality between X-ray absorption and saturation are minimized by using a narrow band filter located at the X-ray tube's collimator.

The narrow band X-ray spectrum emitted from the X-ray tube improves the accuracy of saturation measurements by improving the linearity of the X-ray calibration curves, even though the filtering decreases the signal to noise ratio of the measurements. The resulting decrease in signal-to-noise ratio requires that an optimum X-ray frequency spectrum ("optimum window setting") be experimentally determined for each core sample 16 by comparing the accuracy of the saturation measurements with different X-ray spectrums at several saturation levels.

The procedure for determining the desired wavelengths or optimum window setting is as follows. First, the X-ray power level is selected such that the intensity of the X-ray radiation transmitted through the core when the core is fully saturated with test fluid is enough to be easily detected by the detector 24. A cross section of the core is then scanned at dry, fully brine-saturated conditions and at residual water saturation conditions. Pulse height distribution curves are then constructed for the core sample 16. These curves are plotted with the plotter 62 via the GPIB bus 27 interfacing the plotter 62 to the personal computer 26. The core sample 16 is then scanned again using various filter window settings and curves are plotted showing oil saturation versus the natural log of emergent X-ray intensities. A filter window setting providing the best degree of linearity in the oil saturation versus X-ray intensity calibration curve is then selected.

The X-ray and microwave measurement techniques for determining oil and water saturations require the use of a calibration curve for either the X-ray or the microwave characteristics. One such calibration curve must be determined before making core saturation measurements. The intensity responses of radiation signals emanating from the core are converted to saturation readings by interpolation with the calibration curve.

Figure 5:
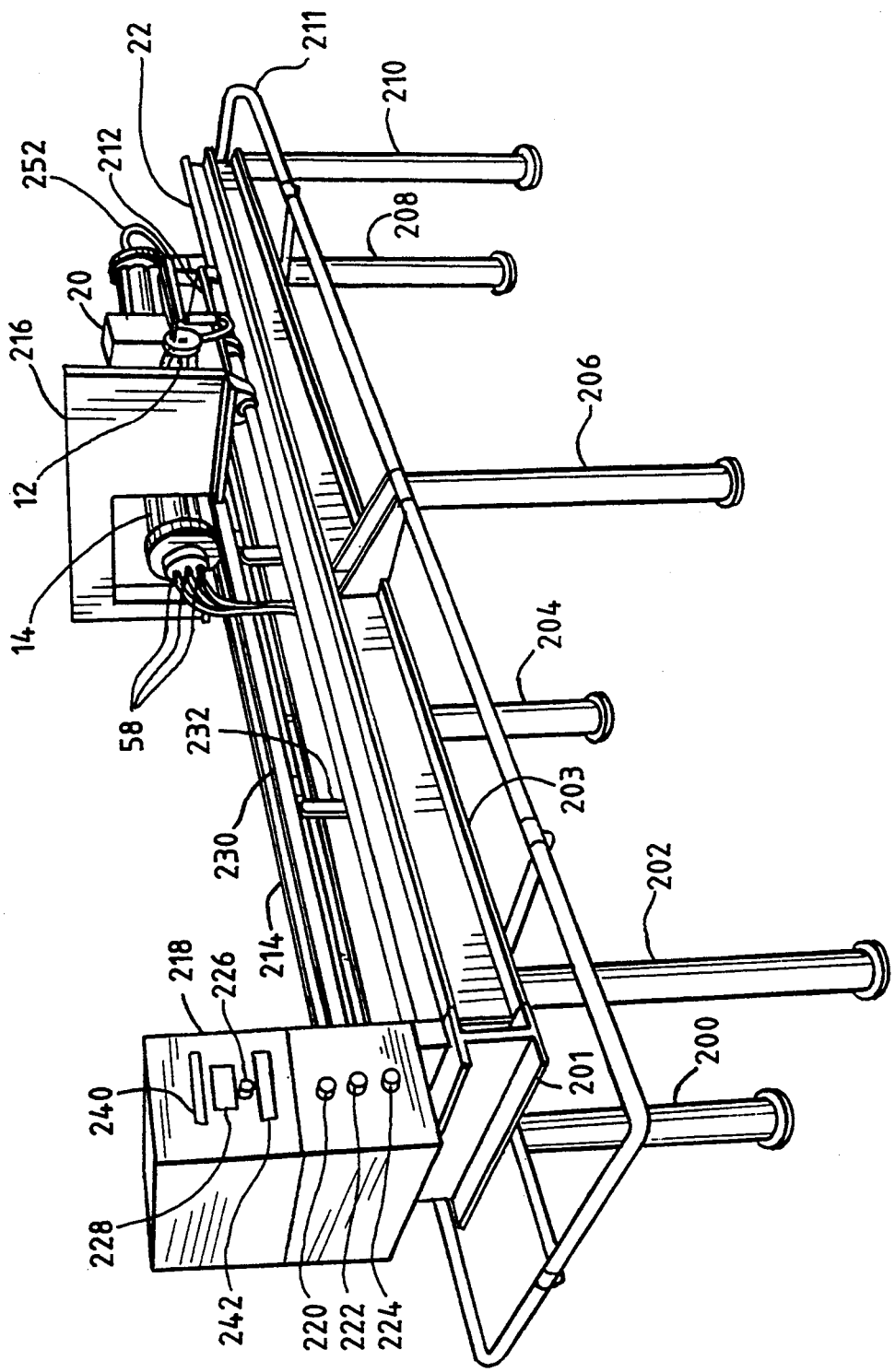
FIG. 5 is a perspective view of a moving table assembly of the apparatus shown in FIG. 3 showing details of microwave emitter and receiver horns and an X-ray emitter and receiver all mounted on a carriage for movement with respect to a core sample being exposed to microwave radiation and X-rays.
Figure 6:
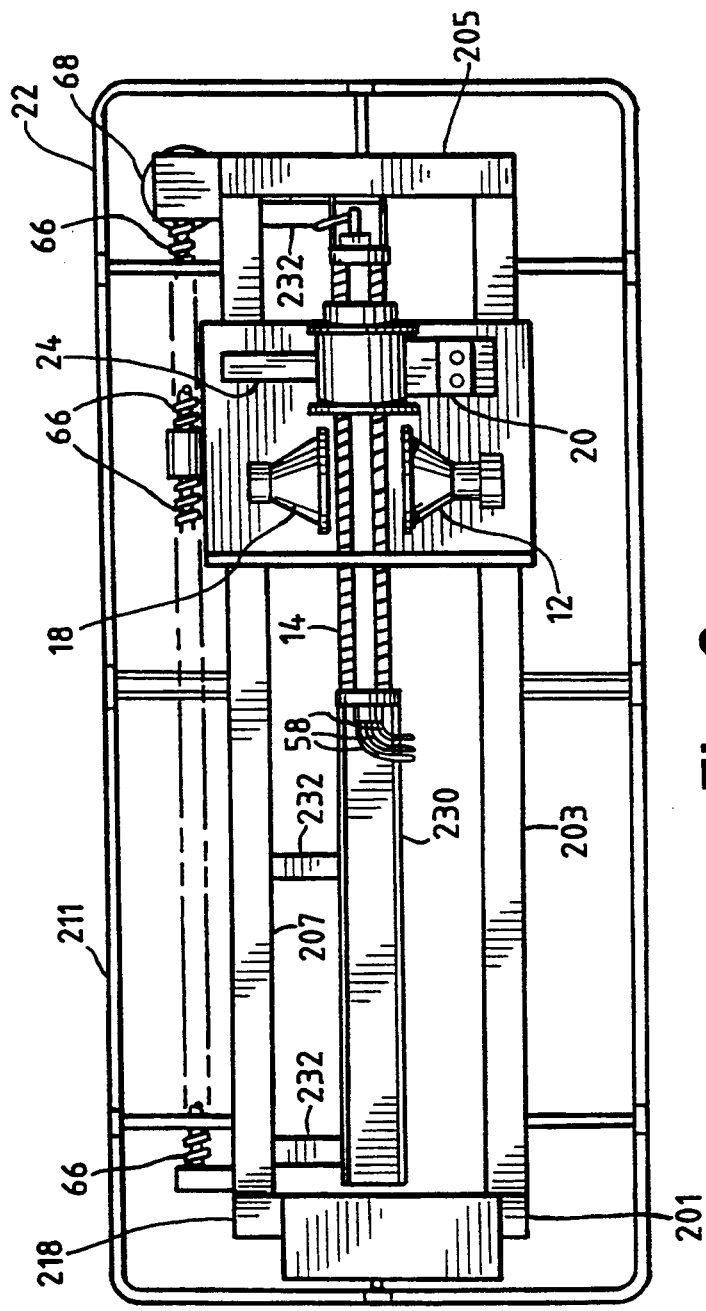
FIG. 6 is a plan view of a moving table assembly of the apparatus of FIG. 5 showing details of the microwave emitter and receiver horns and the X-ray emitter and receiver positioning with respect to the core sample assembly.
Figure 7:
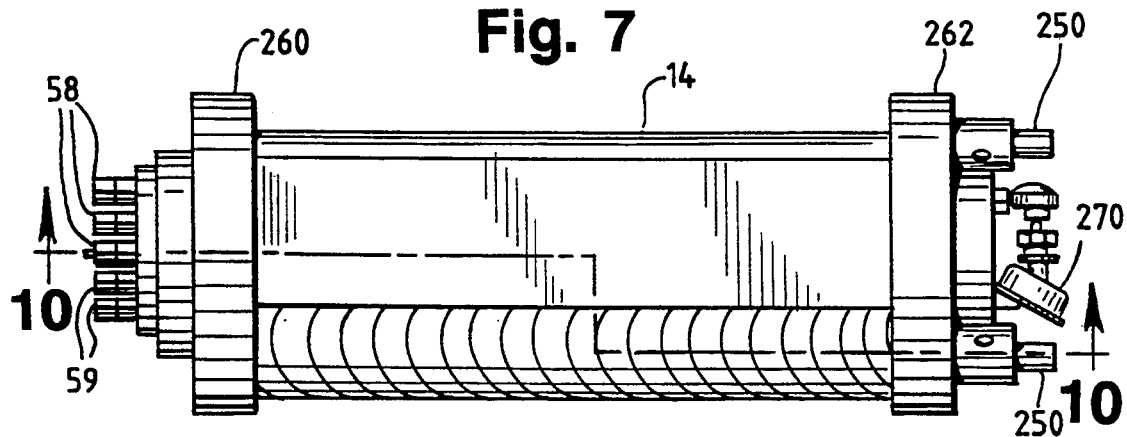
FIG. 7 shows the core sample assembly of FIG. 6.
Figure 11:
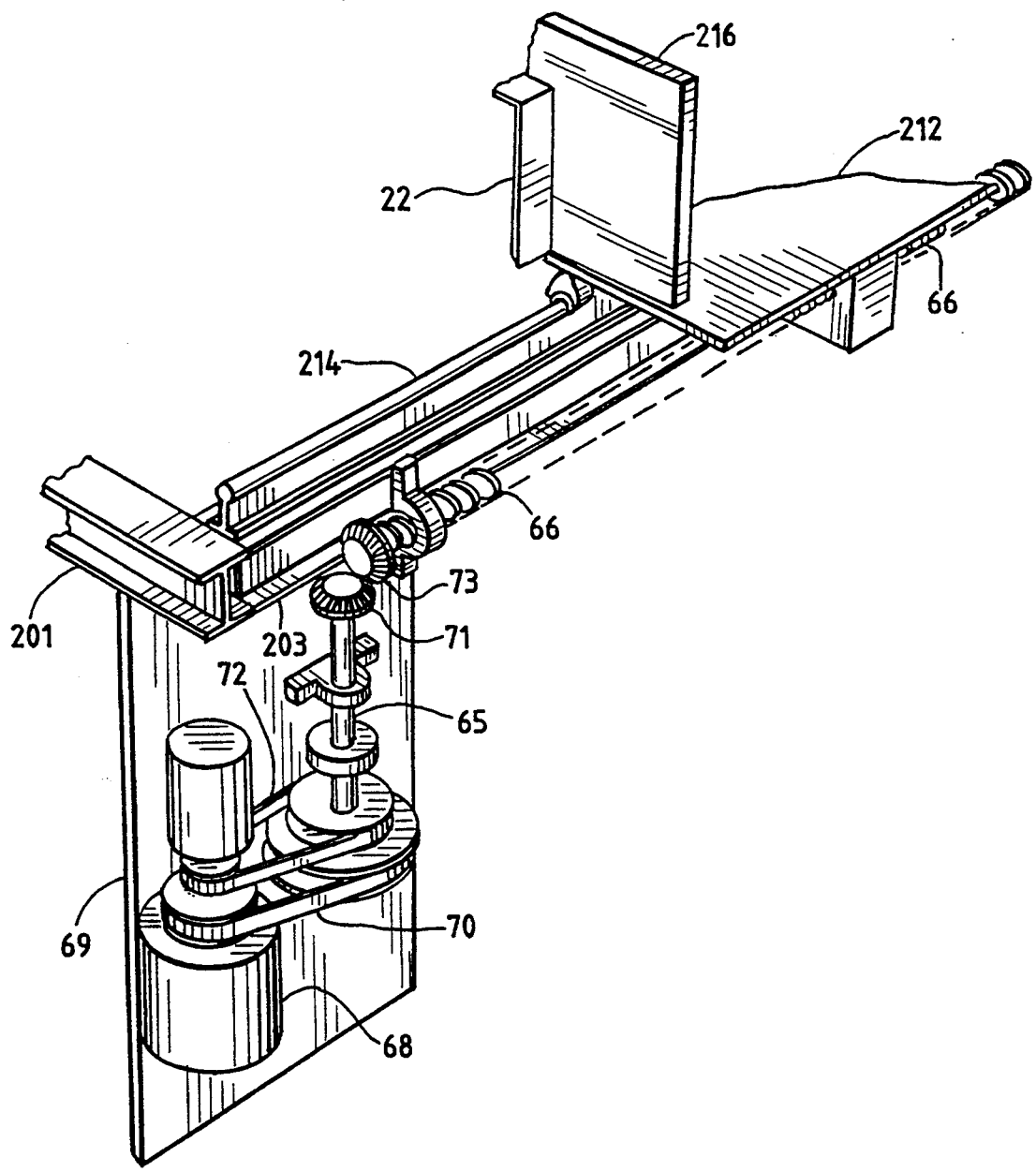
FIG. 11 is a perspective view of a motor and gear assembly for the moving table of FIG. 5 showing details of the motor and screw shaft drive for the moving table.

In order to scan the shielded core holder 14 to provide a profile of the core sample 16 a travelling platform scanning table, moving table 22 (hereinafter referred to as "table 22") provided by Temco is used for this application. The X-ray scanning table, originally designed by Amoco and marketed by Temco, was modified for use in the present invention. The modifications were implemented to allow variable scanning speed and to accommodate the microwave system. The speed and the direction of the X-ray/microwave system is controlled with appropriate software and can be programmed to operate in one of three modes: continuous scan; step scan; and fast scan. The table 22 is illustrated in FIGS. 5 and 6. FIG. 11 illustrates that as a screw drive 66 turns, a moving platform 212 is pushed either forward or backward, depending on screw rotation. The screw drive shaft 66 is driven by motor 68 through the use of the belts 70 and 72. A drive shaft 65 turns a pair of gears 71 and 73 which translate the motor's rotation to the screw drive shaft 66. The motor is supported with a plate 69 which is attached to the table 22. The table 22 can be operated either in the step scan mode or the continuous scan mode. The preferred embodiment of the invention utilizes the table 22 in the step scan mode enabling the X-ray emitter/detector and microwave emitter/detector subsystems to measure fluid saturation levels at intervals along the core sample 16.

The table 22 includes legs 200, 202, 204, 206, 208 and 210. A top support structure for the table 22 is formed from I-beams 201, 203, 205 and 207. A suspended railing 211 surrounds the table 22. The platform 212 holds the X-ray and microwave emitter and detector systems and travels along a pair of tracks 214 which are located on the top of the table 22. The platform 212 has a barrier 216 to shield the table control circuitry (contained in control housing 218) from the X-ray and microwave radiation. Cantilevered posts 232 support a fixed platform 230 which supports the core holder 14. The fixed platform 230 holds the core sample 16 stationary while the core sample 16 is scanned by the X-ray and microwave systems. The front panel of the control housing 218 has control knobs 220, 222 and 224 to manually control the table 22. As stated above, the table 22 has also been modified to provide software control. A meter 228 provides the user with information about the table, and a control knob 226 is associated with the meter 228. Labels 240 and 242 provide the user with information and instructions about the table 22.

The computer 26 illustrated in FIG. 3, is coupled to the microwave detector 18 and the X-ray control unit 23 via the GPIB bus 27 to receive the microwave core intensity signal and the X-ray core intensity signal. The computer 26 using the signals from the X-ray and microwave subsystems then determines the fluid saturations in the core sample 16. Once fluid saturations have been determined, the gas saturation may be determined. The computer 26 then determines the relative permeabilities and saturations of the core sample 16 for given flow rates of oil, water or brine and gas. The brine, oil and gas distributions may be plotted with a plotter 62 or information may be printed with a printer 116.

Software was developed for the automation of data acquisition, analysis and output—including plotting and color graphics. The personal computer 26 enables the user to select routines from a menu. The routines include: X-ray measurement, microwave measurement, set gas flow rate, set liquid flow rate, monitor pressures, direct access to peripherals, access to the pumps, the use of a plotting routine, and access to the personal computer's DOS shell. Equipment automation software 110 provides the menus described. Data acquisition software 112 facilitates communication with each of the peripherals. Data analysis software 114 enables the computer to do additional analysis of the core saturation and permeability measurements. The analysis software also includes the use of a Lotus 1-2-3 spreadsheet. The computer 26 can also communicate with the printer 116 to provide a hard copy of test results.

The porous sandstone or carbonate samples of interest here are selected from a potential EOR site. The core sample 16 is cut out along the bedding plane of the carbonate sandstone sample. After being cut, the core sample is then encapsulated in the core holder 14, as illustrated in FIGS. 7 through 10. The core holder 14 used in the invention is manufactured by Temco (Model No. FCH-10-1). The microwave technique imposes a requirement that the core holder 14 be made of a non-metallic material, so the core holder 14 used in the invention is made from a fibrous composite material. Fibrous materials have transmission characteristics appropriate for use with X-ray and microwave equipment. Also, the core holder 14 can withstand pressures of up to 10,000 psi and temperatures up to 260° F. These temperature and pressure specifications are desired for the purpose of making measurements on the core sample 16 under simulated reservoir conditions.

Figure 8:
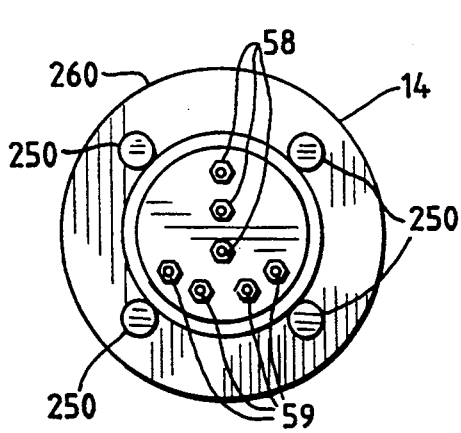
FIG. 8 is an end elevational view of the core sample assembly of FIG. 7 showing the details of the end cap attached thereto for introducing oil, water and gas to the core sample.
Figure 9:
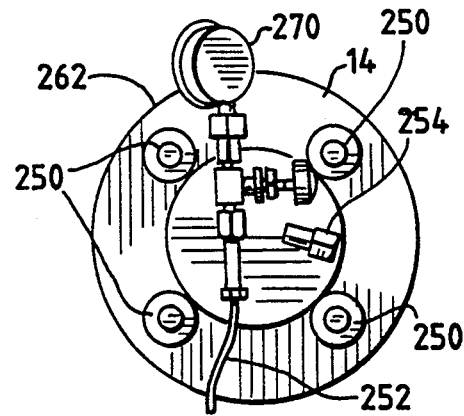
FIG. 9 is an end elevational view of the core sample assembly of FIG. 7 showing the details of the end cap and test meter attached at the outlet end of the core sample.
Figure 10:
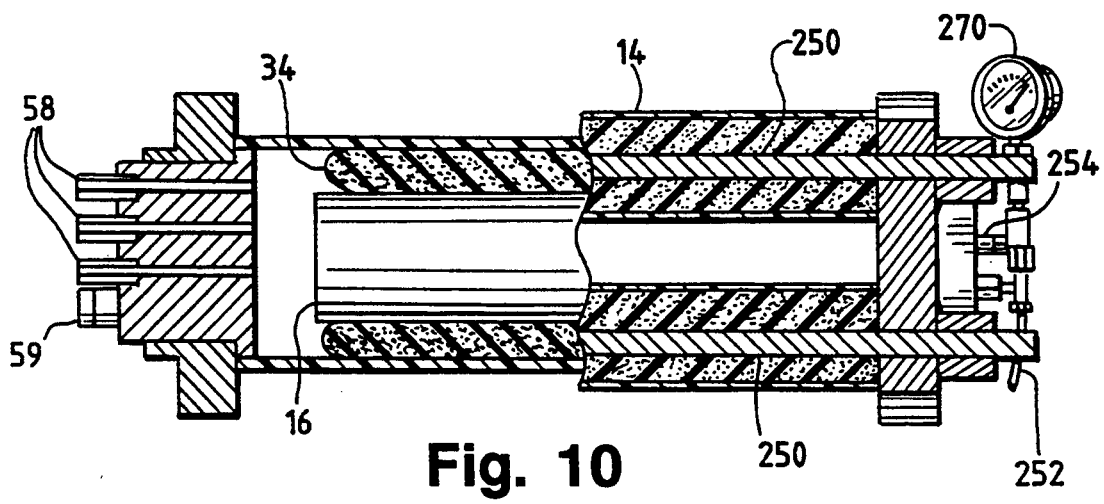
FIG. 10 is a fragmentary cross-sectional view taken through line 10—10 of the core sample assembly of FIG. 7 showing details of the connection of oil, water and gas sources to the core assembly as well as pressure metering taps for sensing pressure drops along the core at selected oil, water and gas flow rates.

In order to determine the volume occupied by the gas in the core sample, it is necessary first to determine the total void volume or empty space within the core sample. This is done by drying the core sample and weighing it to obtain its tare weight. The core sample is then filled with either water or oil and reweighed. The difference between the filled weight and the tare weight, divided by the density of the liquid, yields the void volume of the core sample. The core sample is then flushed and dried before the three phase saturation measurements are made. It may be appreciated that the core cannot be removed after a saturation measurement is complete and weighed to determine the difference between the dry core sample and the wet core sample because the core sample is usually tested under pressure. If it then is removed from the apparatus, the gas under pressure may cause venting of a portion of the water and/or oil which would perturb the results. Thus, the prior art method of simply weighing the core sample after saturation absorption measurements have been made is inadequate. The core holder 14 is supported at its ends with an inlet end plate 260 and an outlet end plate 262. The end plates 260 and 262 are fastened to each other with four connecting rods 250 which extend through the core holder 14. The core holder 14 has channels 58 as illustrated in FIGS. 8 and 10. The channels 58 are used for uniformly injecting three or less fluids into the core at the inlet of the core holder 14. Alternate fluid inlet channels 59 are provided to introduce additional fluids to the core sample 14. Fluids and gases are released from the core holder through outlet lines 252 and 254. A meter 270 measures fluid flow at the outlet of the core holder.

The core sample 16 is suspended by microwave absorptive material 34. Microwave absorptive material increases the accuracy of microwave measurements by preventing the scatter of a signal around the core. A main source of error in measuring microwave loss through the core sample 16 is due to reflected microwaves. Absorptive material 34 prevents reflected microwaves from reaching the microwave detector where they would reduce the signal to noise ratio of microwave measurements. Thus, only microwave radiation which has passed through core sample 16 will arrive at the microwave detector 18.

Before use in the invention the core sample 16 is cleaned and conditioned in situ with pentane and carbon dioxide $CO_2$, then dried with an inert gas such as nitrogen ($N_2$). Pentane in equilibrium with carbon dioxide ($CO_2$) is injected for about two hours at an upstream pressure of 10 to 15 psi. Carbon dioxide alone is then injected for about an hour and a half at 10 to 15 psi injection pressure. Finally, nitrogen gas ($N_2$) is injected continuously for about eight hours at 10 to 15 psi pressure in order to dry the core.

Figure 4:
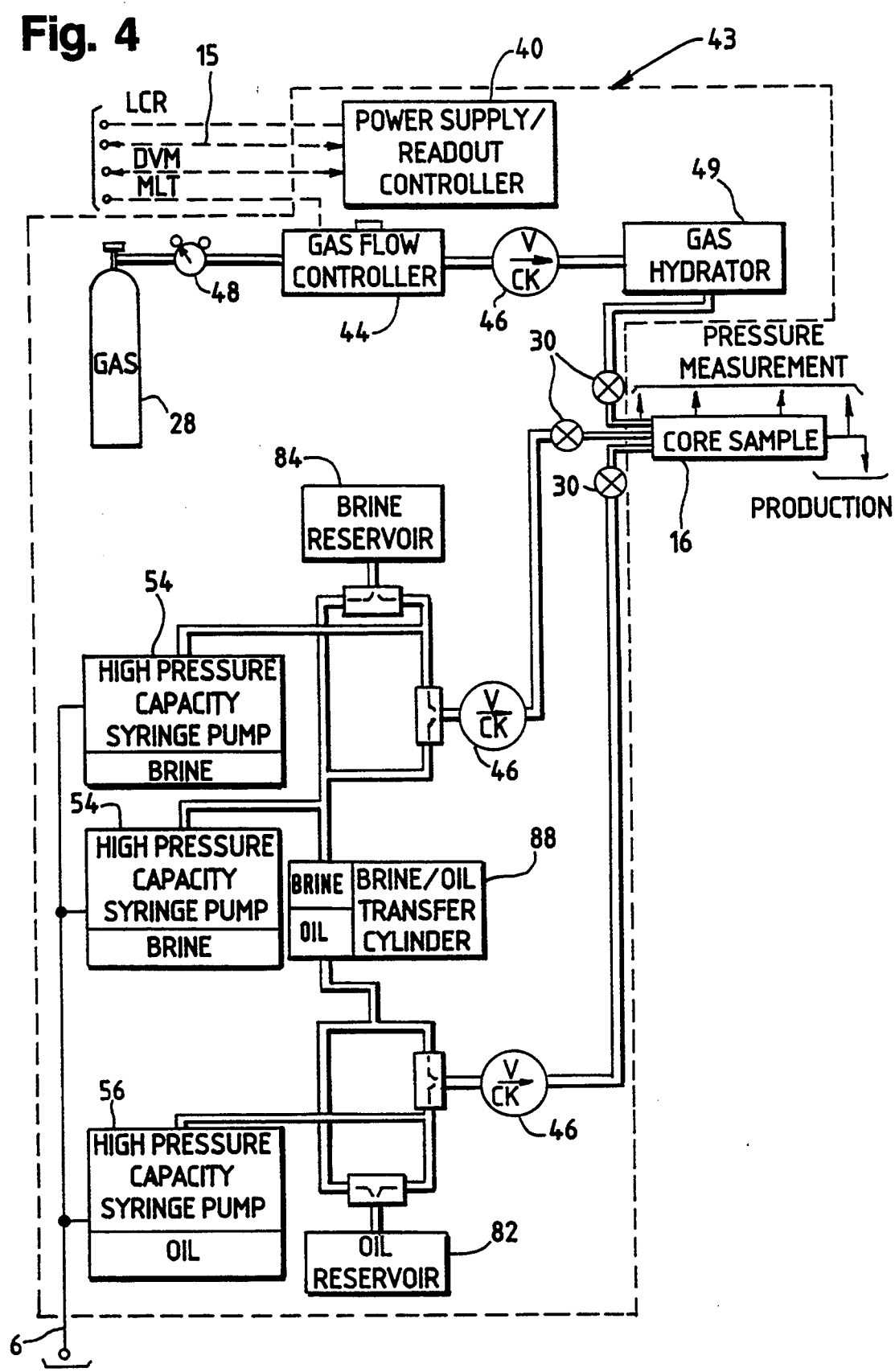
FIG. 4 is a detailed block logic diagram of the core fluid supply of the apparatus shown in FIG. 3 showing the details of the core fluid supply system.

As illustrated in FIG. 3, the gas, oil and water fluids are provided and distributed to the core sample 16 with a core fluid supply 43. A detailed block diagram of the core fluid supply system and its subsystems is shown in FIG. 4. A multiplexer 47 is used to allow a gas flow controller 44, a gas valve subsystem, to attain feedback about gas flow from pressure transducers 60 in order to control the gas flow to the core sample 16. A digital voltmeter (DVM) 45 provides a means to measure various conditions associated with the supply 43.

The nitrogen gas is also used in the three-phase fluid saturation and permeability measurements performed by the apparatus 10. A nitrogen source 28 provides nitrogen gas through a valve 30. A nitrogen gas pump 32 distributes the nitrogen gas within the apparatus 10 and ultimately to the core holder 14 and the core sample 16. The pressure of the injected nitrogen gas is regulated to be from 10 to 15 psi with the nitrogen back pressure regulator 36. Excess nitrogen gas is directed to a reservoir 38.

The flow rate of the gas is controlled by modulating the gas flow controller 44. The valve 30 is a pneumatic control valve (Model 785, Research Control Inc.). The original modulated control signals are generated by the personal computer 26. The modulation signal is then converted to 4 to 20 milliamperes current by the digital-to-analog converter in a power supply/readout controller 40 which is a part of the core fluid supply 43. The controller 40 is an HP-3497A controller manufactured by Hewlett Packard. The controller 40 has an eight channel high voltage actuator which acts as a relay for switching voltages to different devices. The computer 26 communicates with the controller 40 through the GPIB bus 27. Parameter setups and channel measurements are remotely accomplished via the GPIB bus 27 using Hewlett Packard interface bus command codes. The modulated signal supplied to the controller 40 is then used to drive the gas flow controller 44 which operates as a valve to gate the gas supply 28.

The gas flow can be monitored with a gas meter 48. A check valve 46 is provided in the gas supply line as a means to interrupt the gas supply if necessary. Also, the gas must be run through a gas hydrator 49 before being injected into the core sample 16 in order to prevent the gas from stripping water from the brine inside the core 16.

Fluid and gas components 50 (shown in FIG. 1), including methane ($CH_4$), decane, water, or other fluids, are also introduced to the apparatus 10 via the valves 30. The procedure for saturating the core 16 using a high pressure saturation apparatus is similar to the one described in Worthington, A., "A Technique for Detecting Incomplete Saturation of Cores" J Pet Tech., pp. 1716-1717, (Dec. 1978). In this method, the core holder 14 and the core sample 16 are under high pressure in such a fashion as to cause any gas bubbles to be released from the core sample 16. The core sample 16 is then subjected to alternating cycles of strong vacuum from a vacuum pump 52. Next, the core sample 16 is flooded with degassed brine or water, using a water fluid pump 54. The core assembly 16 is then slowly pressurized to 1,000 psi by pumping additional brine or water into the core sample 16.

To examine the effects of flow rates and viscosities on three-phase relative permeability, it was found desirable to perform experiments over a wide range of rates and viscosities. Excessive flow rates or high viscosities were avoided in order to protect the mechanical integrity of the core holder 14. Low flow rates were also avoided to limit the manifestation of end effects. End effects often create anomalies at the interface between the fluids and the core sample in core permeability experiments. The channels 58 and 59 uniformly introduce fluids into the core sample 16 at the inlet of the core holder 14, thus minimizing the end effects. Also, to reduce adverse effects, a compromise was made in the determination of the pressure and rate limits.

Flow Rate Criterion:

$$R_e = \frac{bWk}{6.33 \times 10\mu} \cdot A \leq 0.1 \tag{2}$$

where:
$R_e$=experimental rate limit,
b=turbulence factor, ft$^-$,
W=mass flow rate in pounds per second,
k=permeability in millidarcies (md),
$\mu$=viscosity in centiPoise (cP), and
A=cross-sectional area in ft$^2$.

Core Pressure Criterion:

$$\Delta p \leq 50 \; psig \; (\text{max pressure drop}). \tag{3}$$

The pressure drops along the core sample 16 are measured with pressure transducers 60 as illustrated in FIGS. 1, 2, and 3. The transducers 60 are Validyne pressure transducers. The transducers 60 are interrogated with the controller 40. Pressure transducers 60 have 32 psi full scale plus or minus one-half percent full, with scale linearity and zero shift. The transducers 60 are calibrated against a dead weight tester. FIG. 1 illustrates that the valves 30 may be used with the pressure transducers 60 in order to achieve various combinations of pressure drop distances along the core sample 16. Given the rate of the fluids it is also possible to approximate the pressure drops using Darcy's Law.

Inductance-capacitance-resistance meter 74 (LCR meter) is a Hewlett Packard Model 4262A which enables the apparatus 10 to make resistance measurements along the core sample 16. This facilitates alternative methods of measuring water saturation. Additionally, one may make saturation measurements using volumetric or gravimetric techniques. These alternative techniques serve as a comparison with which to compare the results of the microwave and X-ray measurement techniques. Such comparisons indicate that the accuracy of the saturation measurements attained by the invention is 1% for brine saturations and 1% for oil saturations.

As FIGS. 1, 3 and 4 illustrate in detail, an oil fluid pump 56 is used to inject oil. The fluid pumps 54 and 56 are high pressure capacity syringe pumps. The syringe pumps 54 and 56 negate the need for pulse dampening for each pump. The valves 30, which are four-state three-way valves, are used to facilitate the use of the syringe pumps. Pressure transducer 76 monitors the fluid injection pressure. Pressure relief valves 78 release excess pressure from the fluid injection systems and the back pressure regulator 80 maintains the required 10 to 15 psi pressure in the fluid injection system. The fluid reservoirs 82 and 84 store oil and brine fluids, respectively. Excess gas is released from the fluid injection system using the back pressure regulator 80 via a bubble chamber 86. Oil and brine fluids are injected into the inlet of the core sample 16 with transfer cylinders 88. The transfer cylinders 88 prevent contamination of the pumps 54 and 56. The fluids produced at the outlet of core holder 14 can be visually monitored with a sight glass cell 90.

The sight glass cell is used to measure in situ heavy hydrocarbon condensation. The fluid product is then sampled with a sampling unit 92. The output of the core holder 14 is directed to the sampling unit 92 through the valves 30. The output of the core holder 14 is then passed through a windowed cell separator which separates fluid components from gas components. The windowed cell separator 94 provides a means for stratifying or separating the fluid constituents by their density. Thus, the water or brine is separated from the oil production. An optical examination of the stratification is enabled through the use of the windowed cell separator or gas separator 94. The block diagram in FIG. 3 illustrates an embodiment for separating fluids with a oil/water separator block 120 and fraction collector block 122, which are implemented with the valves 30 and the fluid reservoirs 82 and 84. The fluids are then returned to the core fluid supply system 43.

The gas output directed away from the windowed cell separator 94 can then be directed to a second windowed cell 96 which separates any additional fluids from the gas and allows the gas to be presented to flow meter 98 in order to measure the gas flow. The gas can then be directed to a flow meter 100 or test meter 102 via valves 30. The flow meter 100 will measure the gas flow rate. Alternatively, test meter 102 can be used to measure the nitrogen gas. The gas is then directed away from the apparatus 10 using a vent hood 104. FIG. 4 illustrates a simplified configuration for measuring and monitoring the three-phase output of the core holder 14.

Those skilled in the art will readily appreciate that the apparatus for determining the amounts of water, oil, and gas in a core sample can quickly provide a great deal of information about core permeabilities and saturations. A description of the present forms of the invention have been described by way of example. Variations on the described forms of the apparatus may be made without departing from the invention and the scope of the appended claims.

What is claimed is:

1. An apparatus for determining the amounts of water, oil and gas in a core sample, the core sample having a matrix defining an open space occupied by water, oil and gas including heavy hydrocarbon gas flowing therein, the apparatus comprising:
   a core holder having an inlet, an outlet, and a core sleeve for holding said core sample, the core sleeve being surrounded at least partially by microwave absorptive material for absorbing microwave radiation diffracted around said sleeve thus preventing the diffracted radiation from emerging from the core holder;
   means for illuminating an area of said core sample within the core holder with focused microwave radiation of a known intensity;
   means for adjustably attenuating the microwave radiation to ensure that the power level of the microwave radiation emerging from said core sample is within a measurable range;
   means for measuring the microwave radiation emerging from said core sample to determine the amount of water in said open space of said core sample;
   means for illuminating an area of said core sample within the core holder with ionizing electromagnetic radiation of a known intensity simultaneously with said microwave radiation;
   means for measuring the ionizing electromagnetic radiation transmitted through said core sample to determine the amount of oil in said open space of said core sample;
   information analyzing means, interfaced with said means for measuring microwave radiation and said means for measuring ionizing radiation, for comparing a weight of said core sample without any water or oil therein to said amount of said oil and of said water to determine said amount of gas occupying portions of said open space not occupied by said water and said oil;
   means attached at the outlet of said core holder for optically examining the condensation of heavy hydrocarbon gas and the oil and water flowing from the core sample representative of said gas and the oil and water inside said core sample; and
   means attached at the outlet of said core holder for optically examining the stratification of the water and oil flowing from the core sample representative of said water and oil inside said core sample.

2. An apparatus for determining the amounts of an open space in a core sample occupied by water, oil and gas as defined in claim 1, wherein said means for optically examining the condensation and the oil and water comprises a sight glass cell for measuring the condensation of heavy hydrocarbon gas and the oil and water at the outlet of said core sample facilitating a determination of the activity inside said core sample.

3. An apparatus for determining the amounts of an open space in a core sample occupied by water, oil and gas as defined in claim 1, wherein said means for optically examining the stratification comprises a windowed cell separator for separating, by density, the oil and water at the outlet of said core sample facilitating the measurement of oil and water levels inside said core sample.

4. An apparatus for determining the amounts of an open space in a core sample occupied by water, oil and gas as defined in claim 1, further comprising means for flowing a quantity of said oil through said core sample.

5. An apparatus for determining the amounts of an open space in a core sample occupied by water, oil and gas as defined in claim 1, further comprising means for flowing a quantity of said water through said core sample.

6. An apparatus for determining the amounts of an open space in a core sample occupied by water, oil and gas as defined in claim 1, further comprising means for flowing a quantity of said gas through said core sample.

7. An apparatus for determining the amounts of an open space in a core sample occupied by water, oil and gas as defined in claim 1, further comprising means for flowing a quantity of said gas and a quantity of said oil through said core sample.

8. An apparatus for determining the amounts of an open space in a core sample occupied by water, oil and gas as defined in claim 1, further comprising means for flowing a quantity of said water and a quantity of said oil through said core sample.

9. An apparatus for determining the amounts of an open space in a core sample occupied by water, oil and gas as defined in claim 1, further comprising means for flowing a quantity of said gas, a quantity of said water and a quantity of said oil through said core sample.

10. An apparatus for determining the amounts of an open space in a core sample occupied by water, oil and gas as defined in claims 1, 2, 3, 4, 5, 6, 7, 8 or 9, further comprising means for moving each said means for illuminating and measuring with respect to said core sample to make a plurality of saturation measurements in a short time.

11. A method of determining the amounts of water, oil and gas in a core sample, the core sample having a matrix defining an open space occupied by water, oil and gas including heavy hydrocarbon gas flowing therein, the method comprising steps of:
   illuminating an area of said core sample with focused microwave radiation of a known intensity;
   attenuating the microwave radiation to ensure that the power level of the microwave radiation emerging from said core sample is within a range capable of being measured;
   shielding regions outside the core sample from said microwave radiation to prevent microwave radiation which has not passed through the core sample from being measured;
   measuring microwave radiation emerging from said core sample to determine an amount of water in open space of said core sample;
   illuminating X-rays on said core sample simultaneously with said microwave radiation;
   measuring X-rays emerging from said core sample to determine an amount of oil in said open space of said core sample;

comparing the void volume of said core sample without any water or oil therein to the volume of said amount of oil and the volume of said amount of water to determine the volume of gas occupying portions of said open space not occupied by said water and said oil; and viewing the condensation of heavy hydrocarbon gas and the oil and water flowing from the core sample representative of said gas and the oil and water facilitating a determination of activity inside said core sample.

* * * * *